US009687456B2

(12) United States Patent
Bolster et al.

(10) Patent No.: US 9,687,456 B2
(45) Date of Patent: Jun. 27, 2017

(54) NUTRITIONAL COMPOSITIONS FOR MODULATING INFLAMMATION INCLUDING EXOGENOUS VITAMIN K2

(71) Applicant: NESTEC S.A., Vevey (CH)

(72) Inventors: Douglas Richard Bolster, Eden Prairie, MN (US); Zamzam Kabiry Roughead, Plymouth, MN (US)

(73) Assignee: Nestec S.A., Vevey (CH)

( * ) Notice: Subject to any disclaimer, the term of this patent is extended or adjusted under 35 U.S.C. 154(b) by 42 days.

(21) Appl. No.: 15/099,257

(22) Filed: Apr. 14, 2016

(65) Prior Publication Data

US 2016/0220511 A1 Aug. 4, 2016

Related U.S. Application Data

(62) Division of application No. 13/395,060, filed as application No. PCT/US2010/047468 on Sep. 1, 2010, now abandoned.

(60) Provisional application No. 61/371,846, filed on Aug. 9, 2010, provisional application No. 61/347,945, filed on May 25, 2010, provisional application No. 61/250,847, filed on Oct. 12, 2009, provisional application No. 61/242,087, filed on Sep. 14, 2009.

(51) Int. Cl.
| | |
|---|---|
| *A61K 31/122* | (2006.01) |
| *A61K 31/22* | (2006.01) |
| *A61K 31/593* | (2006.01) |
| *A61K 33/00* | (2006.01) |
| *A61K 33/06* | (2006.01) |
| *A61K 33/26* | (2006.01) |
| *A61K 33/30* | (2006.01) |
| *A61K 33/32* | (2006.01) |
| *A61K 33/34* | (2006.01) |
| *A61K 33/42* | (2006.01) |
| *A61K 45/06* | (2006.01) |
| *A23L 33/00* | (2016.01) |
| *A23L 33/10* | (2016.01) |
| *A23L 33/15* | (2016.01) |
| *A23L 33/16* | (2016.01) |
| *A23L 2/52* | (2006.01) |
| *C12Q 1/68* | (2006.01) |
| *A23L 33/135* | (2016.01) |
| *A23L 33/175* | (2016.01) |

(52) U.S. Cl.
CPC ............ *A61K 31/122* (2013.01); *A23L 2/52* (2013.01); *A23L 33/10* (2016.08); *A23L 33/135* (2016.08); *A23L 33/15* (2016.08); *A23L 33/16* (2016.08); *A23L 33/175* (2016.08); *A23L 33/40* (2016.08); *A61K 31/593* (2013.01); *A61K 33/00* (2013.01); *A61K 33/06* (2013.01); *A61K 33/26* (2013.01); *A61K 33/30* (2013.01); *A61K 33/32* (2013.01); *A61K 33/34* (2013.01); *A61K 33/42* (2013.01); *A61K 45/06* (2013.01); *C12Q 1/6883* (2013.01); *A23V 2002/00* (2013.01); *C12Q 2600/106* (2013.01)

(58) Field of Classification Search
CPC ............................ A61K 31/122; A61K 31/22
USPC ........................................................ 514/681
See application file for complete search history.

(56) References Cited

U.S. PATENT DOCUMENTS

| | | | |
|---|---|---|---|
| 6,566,064 B1 | 5/2003 | Shiraki et al. | |
| 8,138,162 B2 | 3/2012 | Kannar et al. | |
| 2009/0137614 A1 | 5/2009 | Inoue et al. | |
| 2009/0234022 A1 | 9/2009 | Salentine et al. | |

FOREIGN PATENT DOCUMENTS

| | | |
|---|---|---|
| EP | 0689835 | 1/1996 |
| EP | 1153548 A1 | 11/2001 |
| GB | 2370503 | 7/2002 |
| JP | 2004155658 | 6/2004 |
| WO | 97/39746 | 10/1997 |
| WO | 2005/030190 A1 | 4/2005 |
| WO | 2006126541 | 11/2006 |
| WO | 2008/006607 A2 | 1/2008 |
| WO | 2009095240 A1 | 8/2009 |
| WO | WO2009105234 A2 * | 8/2009 |

OTHER PUBLICATIONS

Written Opinion and International Search Report issued Dec. 2, 2010 for corresponding Intl. Appln. No. PCT/US2010/047468.
Li et al., "NF-κB mediates the protein loss induced by TNF-α in differentiated skeletal muscle myotubes" Am J Physiol Regulatory Integrative Comp Physiol, 2000, vol. 279, pp. R1165-R1170.
Japanese Office Action for Application No. P2015-196933, Dispatch No. 372656, Dispatch Date Aug. 23, 2016, 6 pages.
Iwamoto, Jun. " Effect of Vitamin K and Growth Hormone on the Long Bones in Hypophysectomized Young Rats". J. Bone Miner. Metab. (2007) 25:46-53.
Taminiau Review Article: the clinical importance of growth in children with inflammatory bowel disease: is it important to the gastroenterologist? Alimentary Pharmacology and Therapeutics, (Dec. 2007), vol. 26, No. Suppl. 2, pp. 53-56.
JP2004155658 Shunichi et al. 2004 English translation.

(Continued)

Primary Examiner — Jennifer M Kim
(74) Attorney, Agent, or Firm — K&L Gates LLP

(57) ABSTRACT

Nutritional compositions and methods of making and using the nutritional compositions are provided. In a general embodiment, a nutritional composition includes exogenous vitamin K2. The nutritional compositions may further include an additional component selected from the group consisting of phosphorus, magnesium, zinc, iron, copper, manganese, calcium, vitamin D, osteopontin and combinations thereof.

17 Claims, No Drawings

(56) References Cited

OTHER PUBLICATIONS

English Translation of Japanese Office Action for Patent Application No. P2015-196933 mailed Apr. 11, 2017.
Japanese Office Action for Patent Application No. P2015-196933 mailed Apr. 11, 2017.
Cooney, Robert et al. "TNF-binding protein ameliorates inhibition of skeletal muscle protein synthesis during sepsis" The Pennsylvania Sate University College of Medicine, Hershey, Pennsylvania; 1999, pp. E611-E619.
Sato, Toshiro et al. "Comparison of Metabolism of Menaquinone-4 and Menaquinone-7 in Rats" J-Oil Mills, Inc., Vitamins (Japan), 81 (8), 377-381 (2007).

* cited by examiner

NUTRITIONAL COMPOSITIONS FOR MODULATING INFLAMMATION INCLUDING EXOGENOUS VITAMIN K2

PRIORITY CLAIM

This application is a divisional of U.S. patent application Ser. No. 13/395,060 filed Apr. 24, 2012, which is a National Stage of International Application No. PCT/US10/047468 filed Sep. 1, 2010, which claims benefit to Provisional Application Ser. No. 61/371,846 filed Aug. 9, 2010, U.S. Provisional Ser. No. 61/347,945 filed May 25, 2010, U.S. Provisional Application Ser. No. 61/250,847 filed Oct. 12, 2009, and U.S. Provisional Application Ser. No. 61/242,087 filed Sep. 14, 2009, the entire contents of which are incorporated herein by reference.

BACKGROUND

The present disclosure generally relates to health and nutrition. More specifically, the present disclosure relates to nutritional compositions including exogenous vitamin K2 and methods of making and using the nutritional compositions.

There are many types of nutritional compositions currently on the market. Nutritional compositions can be targeted toward certain consumer types, for example, young, elderly, athletic, etc., based on the specific ingredients of the nutritional composition. Nutritional compositions can also be formulated based on the certain physiological conditions that the nutritional compositions are intended to treat or improve.

One goal of nutritional support is to improve bone health by increasing bone density and strength and reducing the incidence of fracture risk. Due to rapidly changing bone densities in children during normal growth and development, or due to underlying medical conditions, children may require nutritional compositions to improve indices of bone health and promote bone growth and bone quality.

SUMMARY

Nutritional compositions having exogenous vitamin K2 and methods of making and using the nutritional compositions are provided. In a general embodiment, the present disclosure provides a nutritional composition including exogenous K2. The nutritional composition can be a complete nutritional or as an oral nutritional supplement (incomplete nutritional). The nutritional composition can be in a formulation designed for any mammal such as a human or an animal. The active ingredients in the nutritional composition can also be provided as a modular product. A modular product can be defined as a method of delivering one or more specific nutrients as a supplement and not intended to be used for sole source nutrition.

In an embodiment, the nutritional composition further includes one or more prebiotics. The prebiotic can be fructooligosaccharides, inulin, lactulose, galactooligosaccharides, acacia gum, soyoligosaccharides, xylooligosaccharides, isomaltooligosaccharides, gentiooligosaccharides, lactosucrose, glucooligosaccharides, pecticoligosaccharides, guar gum, partially hydrolyzed guar gum, sugar alcohols, alpha glucan, beta glucan, or a combination thereof.

In an embodiment, the nutritional composition further includes one or more probiotics. The probiotic can be Saccharomyces, Debaromyces, Candida, Pichia, Torulopsis, Aspergillus, Rhizopus, Mucor, Penicillium, Bifidobacterium, Bacteroides, Clostridium, Fusobacterium, Melissococcus, Propionibacterium, Streptococcus, Enterococcus, Lactococcus, Staphylococcus, Peptostrepococcus, Bacillus, Pediococcus, Micrococcus, Leuconostoc, Weissella, Aerococcus, Oenococcus, Lactobacillus or a combination thereof.

In another embodiment, the nutritional composition further includes one or more amino acids. The amino acid can be Alanine, Arginine, Asparagine, Aspartate, Citrulline, Cysteine, Glutamate, Glutamine, Glycine, Histidine, Hydroxyproline, Hydroxyserine, Hydroxytyrosine, Hydroxylysine, Isoleucine, Leucine, Lysine, Methionine, Phenylalanine, Proline, Serine, Taurine, Threonine, Tryptophan, Tyrosine, Valine, HICA (Alpha-Hydroxyisocaproic Acid), HIVA (Alpha-Hydroxyisovaleric Acid), HIMVA (alpha-hydroxymethylvaleric acid) or a combination thereof.

In an embodiment, the nutritional composition further includes one or more proteins.

In an embodiment, the nutritional composition further includes one or more nucleotides.

In an embodiment, the nutritional composition further includes one or more synbiotics, fish oils, nonmarine omega-3 fatty acid containing dietary fat sources, phytonutrients and/or antioxidants. The antioxidants can be, for example, vitamin A, vitamin $B_1$, vitamin $B_6$, vitamin $B_{12}$, vitamin C, vitamin D, vitamin E, carotenoids, selenium, flavonoids, Lactowolfberry, Goji (wolfberry), polyphenols, lycopene, lutein, lignan, coenzyme Q10 ("CoQ10"), hesperidine and glutathione.

In an embodiment, the nutritional composition is in an administerable form such as pharmaceutical formulations, nutritional formulations, tube-feed formulations, dietary supplements, functional foods, beverage products or a combination thereof.

In another embodiment, the present disclosure provides a method of making a nutritional composition. The method comprises adding exogenous vitamin $K_2$ and a component selected from the group consisting of phosphorus, magnesium, calcium, vitamin D, osteopontin, or combinations thereof to a nutritional composition.

In an alternative embodiment, the present disclosure provides a method of making a nutritional composition. The method comprises adding exogenous vitamin $K_2$ and a component selected from the group consisting of phosphorous, magnesium, zinc, iron, copper, manganese, calcium, vitamin D, osteopontin or combinations thereof to a nutritional composition.

In yet another embodiment, the present disclosure provides a method of improving bone health (i.e. growth, mineralization, microarchitecture, bone organic matrix constituents, density, elasticity and strength) in pediatric patients. The method comprises administering to a child in need of same a nutritional composition including an effective amount of exogenous vitamin $K_2$. The nutritional composition may further include a component selected from the group consisting of phosphorous, magnesium, zinc, iron, copper, manganese, calcium, vitamin D, osteopontin or combinations thereof.

In still another embodiment, the present disclosure provides a method of promoting bone growth and bone quality in a pediatric patient having an underlying medical condition. The method comprises administering to a pediatric patient having an underlying medical condition a nutritional composition including an effective amount of exogenous vitamin $K_2$.

In another embodiment, the present disclosure provides a method of reducing the risk of bone fracture in a pediatric patient. The method comprises administering to a pediatric patient at risk of bone fracture a nutritional composition including an effective amount of exogenous vitamin $K_2$.

In another embodiment, the present disclosure provides a method for improving skeletal muscle health (i.e. metabolic function, lean body mass and mobility). The method comprises administering to a patient who can benefit from improved skeletal muscle health a nutritional composition including an effective amount of exogenous vitamin $K_2$.

An advantage of the present disclosure is to provide an improved nutritional composition having exogenous vitamin $K_2$.

Another advantage of the present disclosure is to provide a method of making an improved nutritional composition.

Yet another advantage of the present disclosure is to provide a nutritional composition that promotes bone health.

Another advantage of the present disclosure is to provide a nutritional composition that promote bone growth and bone quality in patients having underlying medical conditions.

Still another advantage of the present disclosure is to provide a nutritional composition that minimizes bone fracture risk.

Additional features and advantages are described herein, and will be apparent from the following Detailed Description.

DETAILED DESCRIPTION

Maintenance of bone health is essential for mobility and the bone matrix is an important reservoir for critical minerals. On average, 90 percent of peak bone mass is acquired by the age of 18 for women and 20 for men. As such, it is important to promote proper bone health and bone growth and bone quality during the period of normal growth and development in children prior to these ages. Given the accelerated rate of bone accretion during the adolescent period, providing essential nutrients ensures the optimal functioning of the bone formation process. Further, failure to promote bone mineral density during this critical period can lead to decreased bone strength and bone tissue microarchitecture, which can elicit the onset of fragility fractures in the pediatric population.

During childhood bones grow because resorption (the process of breaking down bone) occurs inside the bone while formation of new bone occurs on its outer (periosteal) surface. At puberty the bones get thicker because formation can occur on both the outer and inner (endosteal) surfaces. The remodeling process occurs throughout life and becomes the dominant process by the time that bone reaches its peak mass (typically by the early 20s). In remodeling, a small amount of bone on the surface of trabeculae or in the interior of the cortex is removed and then replaced at the same site. The remodeling process does not change the shape of the bone, but it is nevertheless vital for bone health. Modeling and remodeling continue throughout life so that most of the adult skeleton is replaced about every 10 years. While remodeling predominates by early adulthood, modeling can still occur particularly in response to weakening of the bone.

While Calcium and vitamin D are important nutrients for the development of the inorganic matrix of the bone, several nutrients are needed for normal development of the organic matrix of bone. Specifically, adequate vitamin K, and trace minerals such as zinc, copper, iron nutriture are required for the normal metabolism of noncollagenous proteins such as osteocalcin, osteopontin. Provision of these nutrients during rapid growth, can lead to prevention of osteomalacia and osteoporosis later in life. This improves quality of life and also will save healthcare costs related to hip fractures.

Vitamin K denotes a group of lipophilic, hydrophobic and essential vitamins having a common chemical ring structure (napthoquinone). The two most important forms of vitamin K are vitamin $K_1$, a single compound known as phylloquinone or phytomenadione, and vitamin $K_2$, a series of vitamers known as menaquinones or menatetrenones. There are also several synthetic forms of vitamin K including, for example, vitamins $K_3$, $K_4$ and $K_5$.

Vitamin $K_1$ is the major form of vitamin K in a normal diet and is synthesized by plants including, for example, certain plant oils such as canola and soybean and in green leafy vegetables such as spinach, swiss chard, broccoli, cabbage, cauliflower, kale, and brussels sprouts.

Vitamin $K_2$ is a group of compounds called menaquinones ("MK") having side chains composed of a variable number of unsaturated isoprenoid residues generally designated as MK-n, where n specifies the number of isoprenoids. The most common MKs are MK-4 and MK-7. MK-4 is typically synthesized by animal organs and muscle, while MK-7 is typically synthesized by bacteria during fermentation. Accordingly, MK-7 is particularly abundant in fermented products including cheese, curd cheese and natto (fermented soybeans) and has a particularly long half-life when compared to vitamin $K_1$.

The estimated average requirement for vitamin K in children ages 1 to 18 years in the United States is based upon median intakes of vitamin K for adults. These levels are designed to meet the vitamin K levels required for normal blood coagulation and not other vitamin K-dependent proteins such as osteocalcin. The ratio of undercarboxylated (i.e., inactive) to carboxylated osteocalcin can be a surrogate marker for vitamin K status. Recent evidence suggests that children between the ages of 6 and 18 years of age have elevated levels of undercarboxylated osteocalcin relative to adults. Rather than attempting to increase the intake levels via higher vitamin $K_1$ intake, vitamin $K_2$ allows for administration of a more potent form of vitamin K without negatively impacting parameters of anticoagulation.

As compared to vitamin $K_1$, vitamin $K_2$ provides better absorption and more stable serum levels through a longer half-life. The improved bioavailability of vitamin $K_2$ to extrahepatic tissue may also allow for a greater impact on bone health (i.e. mineralization, microarchitecture and strength) during normal growth and development. Therefore, vitamin $K_2$ provides for a more potent form of the vitamin in which its enhanced bioavailability can impact bone health during normal growth and development.

Additionally, there exists several medical conditions in which bone growth and bone quality in pediatric patients may be compromised. Such conditions may include, for example, developmental delay, failure-to-thrive, neuromuscular dysfunction, severe food allergy and inflammatory bowel disease (e.g., Crohns disease or ulcerative colitis). For example, the incidence of low bone mass in children having inflammatory bowel disease ("IBD") ranges from about 30-50%. Vitamin K is a cited nutrition deficiency in this population and its limited bioavailability may reduce osteocalcin carboxylation as well as reduce bone strength, bone mineralization and bone microarchitecture. Accordingly, children suffering from any of the above-mentioned medical conditions may benefit from a more effective dose of vitamin K.

Rather than attempting to increase the intake levels via higher vitamin K1 intake, Vitamin K2 allows for a more potent form of vitamin K without negatively impacting parameters of anticoagulation. Specifically, vitamin K2 provides better absorption and more stable serum levels through a longer half-life when compared to phylloquinones (vitamin K1). Improved bioavailability of vitamin K2 to extraheptic tissue may allow for a greater impact for improving musculoskeletal health in patients with inflammatory bowel disease (IBD) (Crohn's Disease and Colitis), especially pediatric patients. The incidence of low bone mass ranges from 30-50% in children with IBD. Vitamin K is a cited nutrition deficiency in this population and its limited availability may reduce osteocalcin carboxylation as well as reduce bone strength, bone mineralization and bone microarchitecture. In addition, a low vitamin K status may be a causative factor in Crohn's Disease-associated osteopenia. The osteopenia and elevated rate of bone resorption noted in some Crohn's Disease patients is a multifactorial process and vitamin K deficiency is certainly only one factor in this process. Low vitamin K levels can lead to an increase in the rate of bone resorption, without a compensatory increase in the rate of bone formation. An increased rate of bone turnover is associated with an increased risk of bone loss in Crohn's Disease patients. In terms of nutrition-related etiological factors for osteopenia, there are indications that in patients with longstanding Crohn's Disease, vitamin K deficiency has a greater influence on bone turnover than serum 25(0H) vitamin D concentrations. Vitamin K2 may serve as a critical micronutrient for optimizing bone regulation in this target population.

Further, vitamin $K_2$ may also be effective for bone health in pediatric patients undergoing concurrent drug treatments including, for example, corticosteroids, bisphosphonates or anti-coagulative drugs. Similarly, pediatric patients undergoing biologic therapies or having conditions of gastrointestinal ("GI") impairment including, for example, short bowel syndrome, ulcerative colitis, celiac disease, cystic fibrosis, renal dysfunction and androgen deficiency, gluten intolerance, Crohns disease or severe allergy, may also benefit from administration of nutritional compositions having exogenous vitamin $K_2$.

Applicant has surprisingly found that administering exogenous vitamin $K_2$ as part of a nutritional formulation will improve osteocalcin carboxylation and improve indicies of bone health during normal growth and development in children. Additionally, vitamin $K_2$ supplementation can also promote bone growth and bone quality in pediatric patients with underlying medical conditions in which bone growth and bone quality may be compromised. As a result, Applicant has found that administration of exogenous vitamin $K_2$ increases bone density and improves bone tissue microarchitecture in pediatric patients, thereby reducing the incidence for fracture risk. The effects of vitamin $K_2$ may be seen directly on bone quality such that this form of vitamin K modulates formation of proteins in the organic matrix of the bone involved in microarchitectural morphology, mineralization, density, elasticity and mechanical stiffness, as measured by peripheral quantitative computer tomography ("pQCT") or Dual Energy X-ray absorptiometry ("DEXA"). Vitamin $K_2$ may also be effective for bone health in patients undergoing concurrent drug treatment.

Generally speaking, bone density is expressed as the relationship between bone mass (expressed as the degree of photon attenuation through the bone, or bone mineral content (BMC)) and the image of the bone on a film (i.e., the area) (expressed as $BMC/cm^2$). Additionally, pQCT is a procedure that evaluates peripheral bone in 3 dimensions (volumetric) and is commonly applied to the forearm or tibia. A radiation source (typically x-rays) and a sensor revolve around the bone under examination, which is them reconstructed on the computer screen in a three-dimensional (3-D) image. pQCT is an optimal technique for evaluating bone geometry even though sensitivity varies with the site under evaluation. Unlike most other techniques, pQCT measures true bone density (volumetric mineral bone density) because it normalizes the bone mineral content derived not from the projected area but rather from the volume of the examined bone. pQCT can also be used to calculate the SSI, an index of bone resistance to torsion. The index takes into account bone geometry and the bone's mineral characteristics. See, Geometry and bone density, Radetti, G., et al., Panminerva Med 2006; 48:181-6.

DEXA is based on x-ray spectrometry and it's fundamental principle is based on the degree of attenuation of x-rays emitted from 2 different sources of energy. DEXA is normally used to evaluate lumbar or proximal femoral bone mineralization. DEXA has an accuracy of 4-10% and a coefficient of variation of 1-1.5%. See, Id.

Accordingly, the present disclosure relates to nutritional compositions including exogenous $K_2$ and methods of making and using the nutritional compositions. The present disclosure also relates to the use of pQCT and DEXA to measure bone density and bone tissue microarchitecture. Embodiments of the nutritional compositions of the present disclosure can promote the increase of bone density, mineralization and mechanical stiffness as well as improved bone tissue microarchitecture while minimizing potentially negative effects on blood coagulation and risk of bone fracture. Thus, the use of exogenous vitamin $K_2$ may allow for increase bone health and its associated benefits in pediatric patients. Using pQCT and DEXA, as described above, it is possible to accurately measure bone density and bone microarchitecture to demonstrate the effects of the presently claimed nutritional compositions.

In a general embodiment, the present disclosure provides a nutritional composition including exogenous vitamin $K_2$. The nutritional composition may further include a component selected from the group consisting of phosphorus, magnesium, zinc, iron, copper, manganese, calcium, vitamin D, osteopontin and combinations thereof.

As used herein, the term "nutritional composition" includes, but is not limited to, complete nutritional compositions, partial or incomplete nutritional compositions, and disease or condition specific nutritional compositions. A complete nutritional composition (i.e., those which contain all the essential macro and micro nutrients) can be used as a sole source of nutrition for the patient. Patients can receive 100% of their nutritional requirements from such complete nutritional composition. A partial or incomplete nutritional composition does not contain all the essential macro and micro nutrients and cannot be used as a sole source of nutrition for the patient. Partial or incomplete nutritional compositions can be used as a nutritional supplement. A disease or condition specific nutritional composition is a composition that delivers nutrients or pharmaceuticals and can be a complete or partial nutritional composition.

The exogenous vitamin $K_2$ can be combined with other ingredients for promotion of bone growth and bone quality. For example, exogenous vitamin $K_2$ could work more effectively to support bone health in pediatric patients when used in combination with a component selected from the group consisting of phosphorus, magnesium, zinc, iron, copper, manganese, calcium, vitamin D, osteopontin and combinations thereof. Exogenous vitamin $K_2$ may also work more effectively to support bone health when used in combination with amino acids (e.g., leucine), protein with low sulfurcontaining amino acid content, lipids (n3:n6), bioactive peptides, protease inhibitors, creatine, etc.

In an embodiment, the nutritional composition further includes one or more prebiotics. As used herein, a prebiotic is a selectively fermented ingredient that allows specific changes, both in the composition and/or activity in the gastrointestinal microflora, that confers benefits upon host well-being and health. Non-limiting examples of prebiotics include fructooligosaccharides, inulin, lactulose, galactooligosaccharides, acacia gum, soyoligosaccharides, xylooligosaccharides, isomaltooligosaccharides, gentiooligosaccharides, lactosucrose, glucooligosaccharides, pecticoligosaccharides, guar gum, partially hydrolyzed guar gum, sugar alcohols, alpha glucan, beta glucan, or a combination thereof.

In an embodiment, the nutritional composition further includes one or more probiotics. As used herein, probiotic micro-organisms (hereinafter "probiotics") are preferably microorganisms (alive, including semi-viable or weakened, and/or non-replicating), metabolites, microbial cell preparations or components of microbial cells that could confer health benefits on the host when administered in adequate amounts, more specifically that beneficially affect a host by improving its intestinal microbial balance, leading to effects on the health or well-being of the host. In general, it is believed that these micro-organisms inhibit or influence the growth and/or metabolism of pathogenic bacteria in the intestinal tract. The probiotics may also activate the immune function of the host. For this reason, there have been many different approaches to include probiotics into food products. Non-limiting examples of probiotics include *Saccharomyces, Debaromyces, Candida, Pichia, Torulopsis, Aspergillus, Rhizopus, Mucor, Penicillium, Bifidobacterium, Bacteroides, Clostridium, Fusobacterium, Melissococcus, Propionibacterium, Streptococcus, Enterococcus, Lactococcus, Staphylococcus, Peptostrepococcus, Bacillus, Pediococcus, Micrococcus, Leuconostoc, Weissella, Aerococcus, Oenococcus, Lactobacillus* or a combination thereof.

In another embodiment, the nutritional composition further includes one or more amino acids. Non-limiting examples of amino acids include Alanine, Arginine, Asparagine, Aspartate, Citrulline, Cysteine, Glutamate, Glutamine, Glycine, Histidine, Hydroxyproline, Hydroxyserine, Hydroxytyrosine, Hydroxylysine, Isoleucine, Leucine, Lysine, Methionine, Phenylalanine, Proline, Serine, Taurine, Threonine, Tryptophan, Tyrosine, Valine, HICA (Alpha-Hydroxyisocaproic Acid), HIVA (Alpha-Hydroxyisovaleric Acid), HIMVA (alpha-hydroxymethylvaleric acid) or a combination thereof In a preferred embodiment, non-limiting examples of amino acids include proline, hydroxyproline, hydroxytyrosine, hydroxylysine and hydroxyserine and combinations thereof.

In an embodiment, the nutritional composition further includes one or more proteins.

In an embodiment, the nutritional composition further includes one or more nucleotides.

In an embodiment, the nutritional composition further includes one or more synbiotics, fish oils, nonmarine omega-3 fatty acid containing dietary fat sources, Bowman Birk Inhibitor, phytonutrients and/or antioxidants. As used herein, a synbiotic is a supplement that contains both a prebiotic and a probiotic that work together to improve the microflora of the intestine. Non-limiting examples of fish oils include docosahexaenoic acid ("DHA") and eicosapentaenoic acid ("EPA"). Non-limiting examples of phytonutrients include quercetin, curcumin and limonin. Antioxidants are molecules capable of slowing or preventing the oxidation of other molecules. Non-limiting examples of antioxidants include vitamin A, carotenoids, vitamin C, vitamin E, selenium, flavonoids, Lactowolfberry, Goji (wolfberry), polyphenols, lycopene, lutein, lignan, coenzyme Q10 ("CoQ10"), hesperidine and glutathione.

In another embodiment, the present disclosure provides a method of making a nutritional composition. The method comprises adding an effective amount of exogenous $K_2$ and a component selected from the group consisting of phosphorus, magnesium, zinc, iron, copper, manganese, calcium, vitamin D, osteopontin or combinations thereof to a nutritional composition, for example, to improve bone health of pediatric patients. The nutritional composition can be in an administerable form such as pharmaceutical formulations, nutritional formulations, tube-feed formulations, dietary supplements, functional foods, beverage products or a combination thereof In another embodiment, the present disclosure provides a method of tailoring a treatment or dosage to a patient based on a genetic predisposition as a parameter to assess when determining the potential for Vitamin K2 to impact bone health. Supplementation with Vitamin K2 may be more effective in individuals carrying unique genotypes.

As used herein, a "tube feed" formulation is preferably a complete or incomplete nutritional product that is administered to an animal's gastrointestinal system, other than through oral administration, including but not limited to a nasogastric tube, orogastric tube, gastric tube, jejunostomy tube (J-tube), percutaneous endoscopic gastrostomy (PEG), port, such as a chest wall port that provides access to the stomach, jejunum and other suitable access ports.

As used herein, "effective amount" is preferably an amount that prevents a deficiency, treats a disease or medical condition in an individual or, more generally, reduces symptoms, manages progression of the diseases or provides a nutritional, physiological, or medical benefit to the individual. A treatment can be patient- or doctor-related. In addition, while the terms "individual" and "patient" are often used herein to refer to a human, the invention is not so limited. Accordingly, the terms "individual" and "patient" refer to any animal, mammal or human having or at risk for a medical condition that can benefit from the treatment.

As used herein, animals include, but is not limited to mammals, which include, but is not limited to rodents, aquatic mammals, domestic animals such as dogs and cats, farm animals such as sheep, pigs, cows and horses, and humans. Wherein the terms animal or mammal or their plurals are used, it is contemplated that it also applies to any animals that are capable of the effect exhibited or intended to be exhibited by the context of the passage.

As used herein, "complete nutrition" are preferably nutritional products that contain sufficient types and levels of macronutrients (protein, fats and carbohydrates) and micronutrients to be sufficient to be a sole source of nutrition for the animal to which it is being administered to.

As used herein, "incomplete nutrition" are preferably nutritional products that do not contain sufficient levels of macronutrients (protein, fats and carbohydrates) or micronutrients to be sufficient to be a sole source of nutrition for the animal to which it is being administered to.

As used herein, "Long term administrations" are preferably continuous administrations for more than 6 weeks.

As used herein, mammal preferably includes but is not limited to rodents, aquatic mammals, domestic animals such as dogs and cats, farm animals such as sheep, pigs, cows and horses, and humans. Wherein the term mammal is used, it is contemplated that it also applies to other animals that are capable of the effect exhibited or intended to be exhibited by the mammal.

The term "microorganism" is meant to include the bacterium, yeast and/or fungi, a cell growth medium with the microorganism or a cell growth medium in which microorganism was cultivated.

As used herein, a "Prebiotic" is preferably a food substances that selectively promote the growth of beneficial bacteria or inhibit the growth of pathogenic bacteria in the intestines. They are not inactivated in the stomach and/or upper intestine or absorbed in the GI tract of the person ingesting them, but they are fermented by the gastrointestinal microflora and/or by probiotics. Prebiotics are for example defined by Glenn R. Gibson and Marcel B. Roberfroid, Dietary Modulation of the Human Colonic Microbiota: Introducing the Concept of Prebiotics, J. Nutr. 1995 125: 1401-1412.

As used herein, "Short term administrations" are preferably continuous administrations for less than 6 weeks.

As used herein, the terms "treatment", "treat" and "to alleviate" is preferably to both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The terms "treatment" and "treat" also refer to the maintenance and/or promotion of health in an individual not suffering from a disease but who may be susceptible to the development of an unhealthy condition, such as nitrogen imbalance or muscle loss. The terms "treatment", "treat" and "to alleviate" are also intended to include the potentiation or otherwise enhancement of one or more primary prophylactic or therapeutic measure.

As used herein, a synbiotic is a supplement that contains both a prebiotic and a probiotic that work together to improve the microflora of the intestine.

As used herein, "normal bone growth" preferably includes: during childhood and adolescence bones are sculpted by modeling, which allows for the formation of new bone at one site and the removal of old bone from another site within the same bone. This process allows individual bones to grow in size (linear growth and circumferential growth) and to shift in space. During childhood bones grow because resorption (the process of breaking down bone) occurs inside the bone while formation of new bone occurs on its outer (periosteal) surface. At puberty the bones get thicker because formation can occur on both the outer and inner (endosteal) surfaces. The remodeling process occurs throughout life and becomes the dominant process by the time that bone reaches its peak mass (typically by the early 20s). In remodeling, a small amount of bone on the surface of trabeculae or in the interior of the cortex is removed and then replaced at the same site. The remodeling process does not change the shape of the bone, but it is nevertheless vital for bone health. Modeling and remodeling continue throughout life so that most of the adult skeleton is replaced about every 10 years. While remodeling predominates by early adulthood, modeling can still occur particularly in response to weakening of the bone.

As used herein, a "nucleotide" is preferably understood to be a subunit of deoxyribonucleic acid ("DNA") or ribonucleic acid ("RNA"). It is an organic compound made up of a nitrogenous base, a phosphate molecule, and a sugar molecule (deoxyribose in DNA and ribose in RNA). Individual nucleotide monomers (single units) are linked together to form polymers, or long chains. Exogenous nucleotides are specifically provided by dietary supplementation. The exogenous nucleotide can be in a monomeric form such as, for example, 5' Adenosine Monophosphate ("5'-AMP"), 5'-Guanosine Monophosphate ("5'-GMP"), 5'-Cytosine Monophosphate ("5'-CMP"), 5'-Uracil Monophosphate ("5'-UMP"), 5'-Inosine Monophosphate ("5'-IMP"), 5'-Thymine Monophosphate ("5'-TMP") or a combination thereof. The exogenous nucleotide can also be in a polymeric form such as, for example, an intact RNA. There can be multiple sources of the polymeric form such as, for example, yeast RNA.

Nutritional products are preferably understood to further include any number of additional ingredients, including, for example one or more, vitamin, mineral, sugar, a pharmaceutically acceptable carrier, excipient, flavor agent, or colorants.

The term "protein", "peptide", "oligopeptides" or "polypeptide" as used herein is preferably understood to refer to any composition that includes, a single amino acids (monomers), two or more amino acids joined together by a peptide bond (dipeptide, tripeptide, or polypeptide), collagen, precursor, homolog, analog, mimetic, salt, prodrug, metabolite, or fragment thereof or combination. For the sake of clarity, the use of any of the above terms is interchangeable unless otherwise specified. It will be appreciated that polypeptides (or peptides or proteins or oligopeptides) often contain amino acids other than the 20 amino acids commonly referred to as the 20 naturally occurring amino acids, and that many amino acids, including the terminal amino acids, may be modified in a given polypeptide, either by natural processes such as glycosylation and other post-translational modifications, or by chemical modification techniques which are well known in the art. Among the known modifications which may be present in polypeptides of the present invention include, but are not limited to, acetylation, acylation, ADP-ribosylation, amidation, covalent attachment of a flavanoid or a heme moiety, covalent attachment of a polynucleotide or polynucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycation, glycosylation, glycosylphosphatidyl inositol (GPI) membrane anchor formation, hydroxylation, iodination, methylation, myristoylation, oxidation, proteolytic processing, phosphorylation, prenylation, racemization, selenoylation, sulfation, transfer-RNA mediated addition of amino acids to polypeptides such as arginylation, and ubiquitination. The term "protein" also includes "artificial proteins" which refers to linear or non-linear polypeptides, consisting of alternating repeats of a peptide As used herein, "phytochemicals" or "phytonutrients" are non-nutritive compounds that are found in many foods. Phytochemicals are functional foods that have health benefits beyond basic nutrition, and are health promoting compounds that come from plant sources. As used herein, "Phytochemicals" and "Phytonutrients" refers to any chemical produced by a plant that imparts one or more health benefit on the user. Phytochemicals can be administered by any means, including topically, enterally, and/or parenterally. As used herein, non-limiting examples of phytochemicals and phytonutrients include those that are:

1. Phenolic compounds which include Monophenols (such as: Apiole, Carnosol, Carvacrol, Dillapiole, Rosemarinol); Flavonoids (polyphenols) including Flavonols (such as: Quercetin, (such as: Catechins, (+)-Catechin, (+)-Gallocatechin, (−)-Epicatechin, (−)-Epigallocatechin, (−)-Epigallocatechin gallate (EGCG), (−)-Epicatechin 3-gallate, Theaflavin, Theaflavin-3-gallate, Theaflavin-3'-gallate, Theaflavin-3,3'-digallate, Thearubigins), Anthocyanins (flavonals) and Anthocyanidins (such as: Pelargonidin, Peonidin, Cyanidin, Delphinidin, Malvidin, Petunidin), Isoflavones (phytoestrogens) (such as: Daidzein (formononetin), Genistein (biochanin A), Glycitein), Dihydroflavonols, Chalcones, Coumestans (phytoestrogens), and Coumestrol; Phenolic acids (such as: Ellagic acid, Gallic acid, Tannic acid, Vanillin, Curcumin); Hydroxycinnamic acids (such as: Caffeic acid, Chlorogenic acid, Cinnamic acid, Ferulic acid, Coumarin); Lignans (phytoestrogens), Silymarin, Secoisolariciresinol, Pinoresinol and lariciresinol); Tyrosol esters (such as: Tyrosol, Hydroxytyrosol, Oleocanthal, Oleuropein); Stilbenoids (such as: Resveratrol, Pterostilbene, Piceatannol) and Punicalagins;

2. Terpenes (isoprenoids) which include Carotenoids (tetraterpenoids) including Carotenes (such as: a-Carotene, β-Carotene, γ-Carotene, δ-Carotene, Lycopene, Neurosporene, Phytofluene, Phytoene), and Xanthophylls (such as: Canthaxanthin, Cryptoxanthin, Zeaxanthin, Astaxanthin, Lutein, Rubixanthin); Monoterpenes (such as: Limonene, Perillyl alcohol); Saponins; Lipids including: Phytosterols (such as: Campesterol, beta Sitosterol, gamma sitosterol, Stigmasterol), Tocopherols (vitamin E), and omega-3, 6, and 9 fatty acids (such as: gamma-linolenic acid); Triterpenoid (such as: Oleanolic acid, Ursolic acid, Betulinic acid, Moronic acid);

3. Betalains which include Betacyanins (such as: betanin, isobetanin, probetanin, neobetanin); and Betaxanthins (non glycosidic versions) (such as: Indicaxanthin, and Vulgaxanthin);

4. Organosulfides which include Dithiolthiones (isothiocyanates) (such as: Sulphoraphane); and Thiosulphonates (allium compounds) (such as: Allyl methyl trisulfide, and Diallyl sulfide), Indoles, glucosinolates which include Indole-3-carbinol; sulforaphane; 3,3'-Diindolylmethane; Sinigrin; Allicin; Alliin; Allyl isothiocyanate; Piperine; Syn-propanethial-S-oxide;

5. Protein inhibitors which include protease inhibitors;

6. Other organic acids which include Oxalic acid, Phytic acid (inositol hexaphosphate); Tartaric acid; and Anacardic acid; and 7. combinations thereof.

As used herein the term "antioxidant" is preferably understood to include any one or more of various substances (as beta-carotene (a vitamin A precursor), vitamin C, vitamin E, and selenium) that inhibit oxidation or reactions promoted by Reactive Oxygen Species (ROS) and other radical and non-radical species.

As used herein the term "vitamin" is preferably understood to include any of various fat-soluble or water-soluble organic substances (non-limiting examples include vitamin A, vitamin $B_1$, vitamin $B_6$, vitamin $B_{12}$, vitamin C, vitamin D, vitamin E) essential in minute amounts for normal growth and activity of the body and obtained naturally from plant and animal foods or synthetically made, and include their pro-vitamins, derivatives, and analogs.

As used in this specification and the appended claims, the singular forms "a", "an" and "the" include plural referents unless the context clearly dictates otherwise. Thus, for example, reference to "a polypeptide" includes a mixture of two or more polypeptides, and the like.

As used herein, "about," is preferably understood to refer to numbers in a range of numerals. Moreover, all numerical ranges herein should be understood to include all integer, whole or fractions, within the range.

In an alternative embodiment, the present disclosure provides a method of making a nutritional composition. The method comprises adding exogenous vitamin $K_2$ and a component selected from the group consisting of phosphorous, magnesium, zinc, iron, copper, manganese, calcium, vitamin D, vitamin analogs, osteopontin or combinations thereof to a nutritional composition. In yet another embodiment, the present disclosure provides a method of improving bone health (i.e. growth, mineralization, microarchitecture, bone organic matrix constituents, density, elasticity and strength) in pediatric patients. The method comprises administering to a child in need of same a nutritional composition including an effective amount of exogenous vitamin $K_2$. The nutritional composition may further include a component selected from the group consisting of phosphorous, magnesium, zinc, iron, copper, manganese, calcium, vitamin D, osteopontin or combinations thereof. In still another embodiment, the present disclosure provides a method of promoting bone growth and bone quality in a pediatric patient having an underlying medical condition. The method comprises administering to a pediatric patient having an underlying medical condition a nutritional composition including an effective amount of exogenous vitamin $K_2$. In another embodiment, the present disclosure provides a method of reducing the risk of bone fracture in a pediatric patient. The method comprises administering to a pediatric patient at risk of bone fracture a nutritional composition including an effective amount of exogenous vitamin $K_2$.

The nutritional composition can include the exogenous vitamin $K_2$ in an amount to be administered ranging from about 1 μg/day to about 100 μg/day. The exogenous vitamin $K_2$ can also be administered in an amount ranging from about 10 μg/day to about 95 μg/day, or from about 20 μg/day to about 90 μg/day, or from about 30 μg/day to about 85 μg/day, or from about 50 μg/day to about 80 μg/day, or 1 μg/day, 5 μg/day, or 10 μg/day, or 15 μg/day, or 20 μg/day, or 25 μg/day, or 30 μg/day, or 35 μg/day, or 40 μg/day, or 45 μg/day, or 50 μg/day, or 55 μg/day, or 60 μg/day, or 65 μg/day, or 70 μg/day, or 75 μg/day, or 80 μg/day, or 85 μg/day, or 90 μg/day, 95 μg/day, or 100 μg/day.

By using the nutritional compositions in embodiments of the present disclosure, improved osteocalcin carboxylation and improved indicies of bone health during normal growth and development in children will aid in reducing the risk of bone fracture. Similarly, administration of the present nutritional compositions may also result in increased bioavailability of vitamin K, which can result in increased osteocalcin carboxylation, bone strength, bone mineralization and bone microarchitecture.

In another embodiment, this invention provides for a method for improving skeletal muscle health (i.e. metabolic function, lean body mass and mobility). Skeletal muscle isoenzymes of creatine kinase are sensitive to Vitamin K deficiency. Creatine kinase is a reaction essential to anaerobic energy production. An improvement in Vitamin K status may minimize muscular fatigue and optimize energy production to support anabolic processes such as protein synthesis for muscle mass accretion. Preservation of lean body mass can facilitate the maintenance of functional mobility. The method comprises administering to a patient who can benefit from improved skeletal muscle health a nutritional composition including an effective amount of exogenous vitamin $K_2$.

In another embodiment, this invention provides for a method for reducing inflammation by administering Vitamin K2.

K2 and Inflammation

The acute control of global rates of protein synthesis is predominantly executed at the level of translational initiation with the modulation of various eukaryotic initiation factors (eIFs). The protein kinase referred to as the mammalian target of rapamycin (mTOR), which serves as a convergence point for signaling by growth factors and amino acids to the mRNA binding step of translation initiation is involved in modulation of the phosphorylation of the binding protein for the eukaryotic initiation factor 4E, i.e. 4E-BP1. It also acts to control the phosphorylation status of the 70-kDa ribosomal protein S6 kinase (S6K1). Modulation of these translation initiation events allows for more immediate control of protein synthesis and is responsive to changes associated with acute metabolic or nutritional alterations.

The canonical NF-κB pathway involves nuclear transport of a p65-p50 heterodimer. Activation of NF-κB occurs when IκBs are phosphorylated by the IκB kinase complex, leading to ubiquitination and degradation of IκB and nuclear translocation of the NF-κB dimer. Cytokines such as TNF-α are potent activators of the canonical NF-κB heterodimer, and this activation is associated with muscle protein loss.

Methods

Male Sprague-Dawley rats (175 g) are kept on a 12-h light:dark cycle with food (Harlan-Teklad Rodent Chow, Madison, Wis.) and water provided freely. Animals are administered daily doses of vitamin K2 (MK-7) or saline (control) via oral gavage over 7 days. Stock solutions of vitamin K2 are prepared containing 3.5 g/L HCO-60 and 1 g/L of M&-7 in buffer A (0.15 M NaCl, 0.05 M Tris-HCl, pH 7.5). The K2 is dissolved by sonication during five pulses of 5 set with an amplitude of 6 pm. Solutions thus obtained are clear, homogeneous, and stable. Shortly before vitamin K administration the stock solutions are diluted five times with buffer A, leading to a final HCO-60 concentration of 0.7 g/L. Further dilutions (as required) are made with 0.7 g/L HCO-60 in buffer A. Each dilution step is followed by sonication as described above. In all cases vitamin K2 is administered to the rats in 0.5 mL samples, with either 25 or 50 microgram oral doses.

On the final day (Day 7), rodents are administered vitamin K2 and 2 hours later were given an IP dose of LPS (*Escherichia coli* serotype O111:B4, L2630, Sigma) intraperitoneally (0.5 mg/kg of body weight). Four hours later animals are sacrificed.

Measurement of Protein Synthesis—The fractional rate of synthesis (Ks) is estimated from the rate of incorporation of radioactive phenylalanine into total mixed muscle protein using the specific radioactivity of serum phenylalanine as representative of the precursor pool. The actual time for incorporation of the radiolabeled phenylalanine into protein is taken as the time elapsed from injection until freezing of muscle in liquid nitrogen.

Analysis of mTOR Signaling to eIFs—Gastrocnemius muscles are weighed and homogenized in 7 volumes of buffer containing 20 mM HEPES (pH 7.4), 100 mM potassium chloride, 0.2 mM EDTA, 2 mM EGTA, 50 mM sodium fluoride, 50 mM glycerophosphate, 0.1 mM phenylmethylsulfonyl fluoride, 1 mM benzamidine, 1 mM dithiothreitol (DTT), and 0.5 mM sodium vanadate. The remaining homogenate is centrifuged at 10,000×g for 10 min at 4° C. The resulting supernatant is combined with an equal volume of SDS sample buffer and then subjected to protein immunoblot analysis. Samples are analyzed for the phosphorylation status of 4E-BP1 (Thr37) and ribosomal protein S6 (Ser 235/236), the anti-phosphospecific antibodies were obtained from Cell Signaling Technology, Beverly, Mass. Additionally, samples are analyzed for phosphorylated IKKα/β (Ser176/180; Cell Signaling Technology) and phosphorylated p65 (Ser536; Cell Signaling Technology).

Results

Treatment of rodents with K2 results in a significant decrease in the rise of plasma TNF-a compared to LPS treated animals. Additionally, vitamin K2 results in a significant blunting of the drop in phosphorylation for IKKα/β and NFκB p65 induction compared to LPS treatment. Finally, K2 abrogates the decrease in 4E-BP1(Thr-37) and ribosomal protein S6 phosphorylation compared to LPS treatment along with a greater preservation of the fractional rate of mixed muscle protein synthesis under conditions of inflammatory sepsis.

In another embodiment, this invention provides for a method for reducing inflammation, the method comprising: administering to a patient in need of same a nutritional composition comprising exogenous vitamin K2. In another embodiment, this nutritional composition further comprises a component selected from the group consisting of phosphorus, magnesium, zinc, iron, copper, manganese, calcium, vitamin D, osteopontin and combinations thereof In another embodiment, this nutritional composition further comprises at least one antioxidant. In another embodiment, this nutritional composition further comprises at least one phytonutrient. In another embodiment, the patient is a child.

In another embodiment, this invention provides for a method for reducing the effects of inflammation, the method comprising: administering to a patient in need of same a nutritional composition comprising exogenous vitamin K2. In another embodiment, this nutritional composition further comprises a component selected from the group consisting of phosphorus, magnesium, zinc, iron, copper, manganese, calcium, vitamin D, osteopontin and combinations thereof. In another embodiment, this nutritional composition further comprises at least one antioxidant. In another embodiment, this nutritional composition further comprises at least one phytonutrient. In another embodiment, the patient is a child.

In another embodiment, this invention provides for a method for preventing the effects of inflammation, the method comprising: administering to a patient in need of same a nutritional composition comprising exogenous vitamin K2. In another embodiment, this nutritional composition further comprises a component selected from the group consisting of phosphorus, magnesium, zinc, iron, copper, manganese, calcium, vitamin D, osteopontin and combinations thereof. In another embodiment, this nutritional composition further comprises at least one antioxidant. In another embodiment, this nutritional composition further comprises at least one phytonutrient. In another embodiment, the patient is a child.

In another embodiment, this invention provides for a method for decreasing the rise of plasma TNF-α under conditions of inflammation, the method comprising: administering to a patient in need of same a nutritional composition comprising exogenous vitamin K2. In another embodiment, this nutritional composition further comprises a component selected from the group consisting of phosphorus, magnesium, zinc, iron, copper, manganese, calcium, vitamin D, osteopontin and combinations thereof. In another embodiment, this nutritional composition further comprises at least one antioxidant. In another embodiment, this nutritional composition further comprises at least one phytonutrient. In another embodiment, the patient is a child.

In another embodiment, this invention provides for a method for blunting the drop in phosphorylation for IKKα/β and NFκB p65 induction under conditions of inflammation, the method comprising: administering to a patient in need of same a nutritional composition comprising exogenous vitamin K2. In another embodiment, this nutritional composition further comprises a component selected from the group consisting of phosphorus, magnesium, zinc, iron, copper, manganese, calcium, vitamin D, osteopontin and combinations thereof. In another embodiment, this nutritional composition further comprises at least one antioxidant. In another embodiment, this nutritional composition further comprises at least one phytonutrient. In another embodiment, the patient is a child.

In another embodiment, this invention provides for a method for abrogating the decrease in 4E-BP1(Thr-37) and ribosomal protein S6 phosphorylation under conditions of inflammation, the method comprising: administering to a patient in need of same a nutritional composition comprising exogenous vitamin K2. In another embodiment, this nutritional composition further comprises a component selected from the group consisting of phosphorus, magnesium, zinc, iron, copper, manganese, calcium, vitamin D, osteopontin and combinations thereof In another embodiment, this nutritional composition further comprises at least one antioxidant. In another embodiment, this nutritional composition further comprises at least one phytonutrient. In another embodiment, the patient is a child.

In another embodiment, this invention provides for a method for preserving the fractional rate of mixed muscle protein synthesis under conditions of inflammation, the method comprising: administering to a patient in need of same a nutritional composition comprising exogenous vitamin K2. In another embodiment, this nutritional composition further comprises a component selected from the group consisting of phosphorus, magnesium, zinc, iron, copper, manganese, calcium, vitamin D, osteopontin and combinations thereof In another embodiment, this nutritional composition further comprises at least one antioxidant. In another embodiment, this nutritional composition further comprises at least one phytonutrient. In another embodiment, the patient is a child.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of modulating the effects of inflammation, the method comprising administering a nutritional composition comprising an effective amount of exogenous MK-7 to a patient having cystic fibrosis.

2. The method of claim 1, wherein the effective amount of exogenous MK-7 is from about 1 μg to about 100 μg per day.

3. The method of claim 1, wherein the effective amount of exogenous MK-7 is from about 20 μg to about 90 μg per day.

4. The method of claim 1, wherein the effective amount of exogenous MK-7 is from about 50 μg to about 80 μg per day.

5. The method of claim 1, wherein the nutritional composition is in an administrable form selected from the group consisting of pharmaceutical formulations, nutritional formulations, tube-feed formulations, dietary supplements, functional foods and beverage products.

6. The method of claim 1, the nutritional composition further comprising at least one component selected from the group consisting of prebiotic, probiotics, symbiotic, amino acid, protein, nucleotides, a fish oil, non-marine omega-3 fatty acid containing dietary fat source, phytonutrients, antioxidant, and combinations thereof.

7. The nutritional composition of claim 6, wherein the amino acid is selected from the group consisting of proline, hydroxyproline, hydroxytyrosine, hydroxylysine and hydroxyserine and combinations thereof.

8. The method of claim 1, wherein the modulation of the effects of inflammation is a reducing of the effects of inflammation.

9. The method of claim 1, wherein the modulation of the effects of inflammation is a preventing of the effects of inflammation.

10. The method of claim 1, wherein the modulation of the effects of inflammation is decreasing a rise of plasma TNF-α under conditions of inflammation.

11. The method of claim 1, wherein the modulation of the effects of inflammation is blunting a drop in phosphorylation for IKKα/β and NFκB p65 induction under conditions of inflammation.

12. The method of claim 1, wherein the modulation of the effects of inflammation is abrogating a decrease in 4E-BP1 (Thr-37) and ribosomal protein S6 phosphorylation under conditions of inflammation.

13. The method of claim 1, wherein the modulation of the effects of inflammation is preserving the fractional rate of mixed muscle protein synthesis under conditions of inflammation.

14. The method of claim 1, comprising the steps of:
determining a genetic predisposition of the patient to determine the likely efficacy of treatment with exogenous MK-7; and
if determined to be efficacious, administering to the patient the nutritional composition comprising the effective amount of the exogenous vitamin MK-7 and a component selected from the group consisting of phosphorus, magnesium, zinc, iron, copper, manganese, calcium, vitamin D, osteopontin and combinations thereof.

15. The method of claim 14 wherein the determining of the genetic predisposition comprises determining the genotype.

16. The method of claim 14 wherein the genetic predisposition is used to determine the dosage of the exogenous MK-7.

17. The method of claim 1, wherein the patient is a child.

* * * * *